(12) United States Patent
Ra et al.

(10) Patent No.: US 8,426,370 B2
(45) Date of Patent: Apr. 23, 2013

(54) DIARYL HEPATONOID-BASED COMPOUNDS AND USE THEREOF

(75) Inventors: Jeong Chan Ra, Gyeonggi-do (KR); Young Ho Kim, Daejeon (KR); Hyuk Joon Kwon, Seoul (KR); Huu Tung Nguyen, Daejeon (KR)

(73) Assignee: RNL Bio Co., Ltd., Seoul (KR)

( * ) Notice: Subject to any disclaimer, the term of this patent is extended or adjusted under 35 U.S.C. 154(b) by 190 days.

(21) Appl. No.: 12/996,321

(22) PCT Filed: Jun. 4, 2009

(86) PCT No.: PCT/KR2009/002997
§ 371 (c)(1),
(2), (4) Date: Jan. 13, 2011

(87) PCT Pub. No.: WO2009/148282
PCT Pub. Date: Dec. 10, 2009

(65) Prior Publication Data
US 2011/0098239 A1 Apr. 28, 2011

(30) Foreign Application Priority Data
Jun. 5, 2008 (KR) .......................... 10-2008-0052844

(51) Int. Cl.
*A01N 43/04* (2006.01)
*A61K 31/70* (2006.01)
*C07H 15/00* (2006.01)
*C07H 15/24* (2006.01)

(52) U.S. Cl.
USPC .......................... 514/25; 536/18.1; 536/18.2

(58) Field of Classification Search .......................... None
See application file for complete search history.

(56) References Cited

U.S. PATENT DOCUMENTS
2005/0215635 A1 9/2005 Rafi et al.

FOREIGN PATENT DOCUMENTS
JP 2003-192602 A * 7/2003
KR 10-0721703 B1 5/2007
KR 10-0769050 B1 10/2007

OTHER PUBLICATIONS

Wolff, Manfred E. "Burger's Medicinal Chemistry, 5ed, Part I", John Wiley & Sons, 1995, pp. 975-977.*
Banker, G.S. et al, "Modern Pharmaceutics, 3ed.", Marcel Dekker, New York, 1996, p. 596.*
AN 2007:34685, Lee et al, Natural Product Communications, 2006, 1(6), 461-464.*
T. Akihisa et al., "Triterpene Alcohols and 3-Oxo Steroids of Nine Leguminosae Seeds", Phytochemistry, 1994, pp. 1309-1313, vol. 35, No. 5.
Fingl et al., "The Pharmacological Basis of Therapeutics", Ch. 1, p. 1.
H. Fuchino et al., "Chemical Evaluation of *Betula* Species in Japan. I. Constituents of *Betula ermanii*", Chem. Pharm. Bull., 1995, pp. 1937-1942, vol. 43, No. 11.
A. Hisham et al., "Salacianone and Salacianol, Two Triterpenes From *Salacia beddomei*", Phytochemistry, 1995, pp. 1227-1231, vol. 40, No. 4.
J. Ishida et al., "Antitumor-promoting effects of cyclic diarylheptanoids on Epstein-Barr virus activation and two-stage mouse skin carcinogenesis", Cancer Letters, Oct. 2000, pp. 135-140, vol. 159, No. 2.
J. Ishida et al., "Chemopreventive Potential of Cyclic Diarylheptanoids", Bioorganic Medical Chemistry, Oct. 2002, pp. 3361-3365, vol. 10 No. 10.
W. Kisiel, "Guaianolides From *Picris altissima*", Phytochemistry, 1992, pp. 328-329, vol. 31, No. 1.
Shoei-Sheng Lee et al., "Chemical constituents from *Alnus formosana* burk. II. Polar constituents from the leaves", Natural Product Communications, 2006, pp. 461-464, vol. 1, No. 6.
S. Seo et al., "Biosynthesis of Oleanene- and Ursene-Type Triterpenes from [413C]Mevalonolactone and [1,2-13C2]Acetate in Tissue Cultures of *Isodon japonicas* Hara", J. Am. Chem . Soc., 1981, pp. 2075-2080, vol. 103.
K. Shiojima et al., "Fern Constituents: Two New Secofilicane Triterpenoids From *Adiantum cuneatum*", Chem. Pharm. Bull., 1996, pp. 630-632, vol. 44, No. 3.
M. Tamai et al., "New Hepatoprotective Triterpenes from *Canarium album*", Planta Med., 1989, pp. 44-47, vol. 55.
English Language Abstract of KR 10-0721703 B1, May 2007.
English Language Abstract of KR 10-0769050 B1, Oct. 2007.
International Search Report of PCT/KR2009/002997, Jan. 2010.

* cited by examiner

*Primary Examiner* — Traviss C McIntosh, III
(74) *Attorney, Agent, or Firm* — Rabin & Berdo, P.C.

(57) ABSTRACT

The present invention relates to a diaryl hepatonoid-based compound of formula (1) having viral inhibitory activity; its pharmaceutically acceptable salt; or a hydrate, a solvate or a prodrug of any of the foregoing, and a pharmaceutical composition comprising the same, and the use thereof therapeutic agents. The diaryl hepatonoid-based compounds according to present invention have an excellent effect of inhibiting viral activity, and thus will be useful as therapeutic agents against virus-related diseases.

3 Claims, 2 Drawing Sheets

DIARYL HEPATONOID-BASED COMPOUNDS AND USE THEREOF

FIELD OF INVENTION

Figure 1:
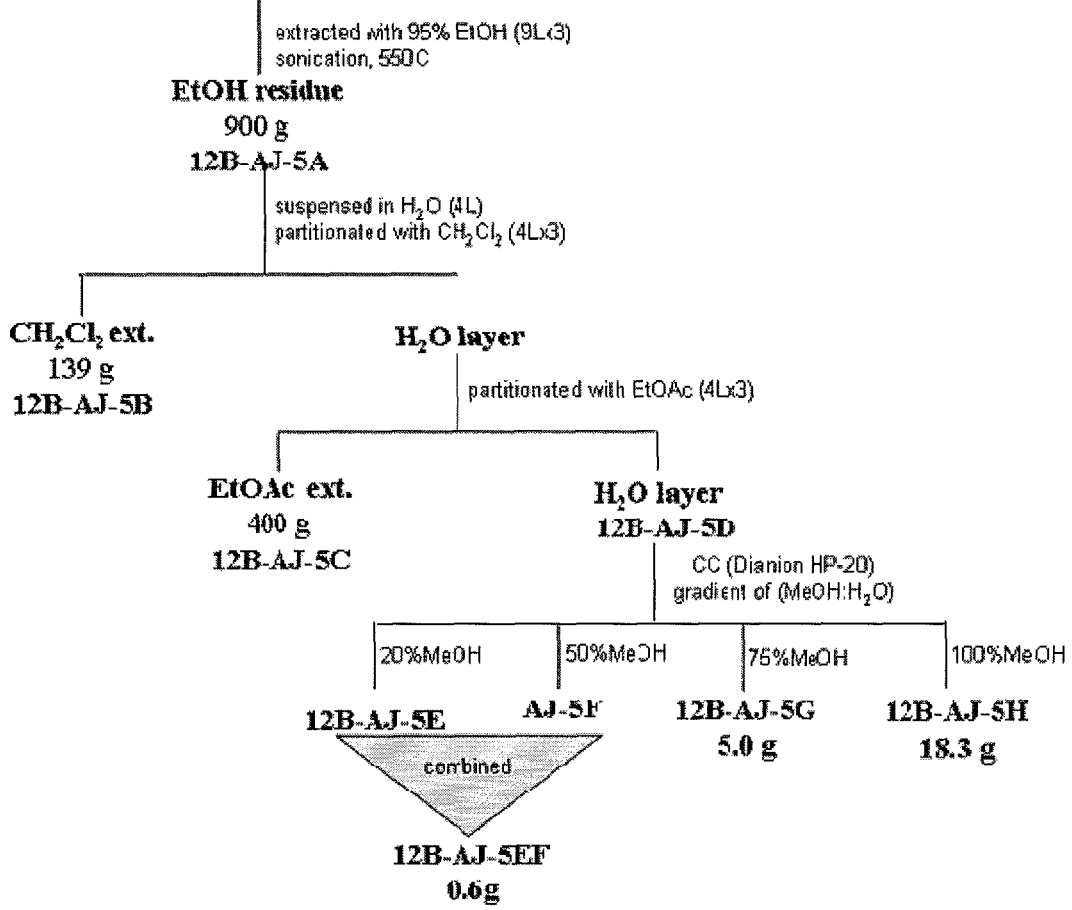

The present invention relates to a novel diaryl hepatonoid-based compound of formula (1) having viral inhibitory activity, or its pharmaceutically acceptable salt, a hydrates, a solvate or a prodrug of any of the foregoing, and a pharmaceutical composition containing the same, and the use thereof therapeutic agents.

BACKGROUND ART

Viruses cause various diseases, and particularly, a typical one among pathogenic viruses that become a problem in the field of stockbreeding is Avian influenza virus. Avian influenza virus belongs to the Orthomyxoviridae family, and causes much damage to poultry, such as hens and turkey. Avian influenza viruses are classified into highly pathogenic avian viruses, low pathogenic avian viruses and non-pathogenic avian viruses according to their pathogenicity. The highly pathogenic avian viruses are classified as "List A species" by the Office International des Epizootics (OIE) and as class I infectious livestock diseases in Korea.

The influenza viruses are classified into three types, A, B and C, according to the antigenic properties of their matrix proteins and nucleocapsid proteins. Moreover, according to the differences in the antigenic structures of haemagglutinin (HA), which assists in host cell receptor binding and the fusion between the host cell membrane and the viral envelop to cause a virus infection, and neuraminidase (NA) which plays an important role when the viruses bud from cells after proliferation, the influenza viruses are further classified into 16 HA and 9 NA subtypes, each. Theoretically, 144 kinds of virus subtypes could exist by the combination of the two proteins.

Infection with Avian influenza virus occurs mainly by direct contact with avian excreta and also spreads by droplets, water, human feet, feeding cars, instruments, devices, feces attached to the outer surface of eggs, and the like. In the symptoms of the viral infection, respiratory symptoms, diarrhea and a rapid decrease in egg production are commonly shown, although the symptoms vary depending on the pathogenicity of infected viruses. In some cases, head portions, such as crests, show cyanosis, and sometimes edema appears on the face or feathers flock together at one point. Mortality caused by the viral infection varies from 0% to 100% depending on the viral pathogenicity. The viral infection requires precise diagnosis because its symptoms are similar to those of other diseases such as Newcastle disease, infectious laryngotracheitis, mycoplasma infections, and the like.

About 23 outbreaks of highly pathogenic avian influenza have been recorded worldwide during 1959-2003, but were mostly localized events. Outbreaks of H5N1 subtype highpathogenic avian influenza that occurred in Korea in December, 2003 occurred in more than 30 countries, including Europe, Africa and most countries in Southeast Asia such as Japan, China, Thailand, Vietnam and Indonesia, thus becoming pandemic.

Although it is known that humans cannot be infected by avian influenza, prevention of avian influenza is being of paramount importance to public health sector due to the case of human infection with H5N1 in Hongkong in 1997, isolation of H9N2 avian influenza viruses from humans in 1999 and human cases of H7 avian influenza infection in Canada in 2004. According to a report of the World Health Organization (WHO) (http://www.who.int/csr/disease/avian_influenza/country/cases_table_2006_06_20/en/index.html), it was confirmed that the 228 persons were infected with H5N1 subtype virus in 10 countries, and 130 persons of them died during a period ranging from 2003 to Jun. 20, 2006. In Korea, since low-pathogenic avian influenza by H9N2 subtype had occurred in 1996, it reoccurred in 1999.

When avian influenza outbreaks occur, most countries respond by killing all of the infected animals involved in the outbreak, and countries experiencing outbreaks cannot export poultry products. Accordingly, avian influenza viruses can be regarded as being among primary factors that interfere with the development of the livestock industry. Furthermore, when there is a risk of human infection, the damage spread to a wide range of industries, including the tourist industry and the transport industry.

Recently, considerable efforts have been made worldwide to develop anti-viral agents. Commercially available antiviral agents include lamibudine that is used for the treatment of HIV (Human Immunodeficiency Virus)-1 and hepatitis B, gancyclovir that is used for the treatment of herpes virus infections, and ribavirin that is used mainly for the treatment of symptoms of respiratory syncytial virus infection but can be used for the treatment of symptoms of various virus infections in emergency. In addition, zanamivir RELENZA™ and oseltamivir, TAMIFLU™ which are synthesized artificially as neuraminidase inhibitors of influenza virus are also commercially available.

However, the use of amantadine and its analogue, rimantadine, which were approved for treatment of influenza virus A, has been limited due to the appearance of resistant virus and its side effect. Recently, virus resistant to oseltamivir among H5N1 avian influenza viruses appeared, and thus, the development of various anti-virus agents is urgently required.

Meanwhile, *Alnus japonica* is a deciduous tree belonging to the genus *Alnus* of the Betulaceae and is commonly called an *Alnus japonica* tree. About 30 species of *Alnus japonica* are distributed in the Northern Hemisphere and the South America, and about 9 species of *Alnus japonica* are distributed in Korea. It grows near swampy areas, its height is about 20 m and its bark is of a deep purplish-brown color. Its winter bud is a long oval shape just like the shape of an egg turned upside down, which has three ridge lines and a peduncle. The leaves of *Alnus japonica* grow alternately, and they are oval shaped, egg-shaped or lanceolate. Both sides of the leaf are lustrous and leaf margins are saw-toothed. The flower of *Alnus japonica* blooms in March to April, is unisexual and forms a catkin. Staminate spike bears staminate flower and each bract has 3-4 flowers. There are four perianths and four stamens in each flower. The fruit ripens in October and 2-6 fruits are produced. It is long egg-shaped and looks like a pine cone.

Meanwhile, triterpenoid-based compounds contain α-amyrin, α-amyrin acetate, baurenol acetate, β-amyrin, β-amyrin acetate, daturaolone germanicol acetate, lupeol acetate, Lup-20(29)-en-3-one, olean-18-en-3-one, and taraxasterol, and sesquiterpenoids include 11,13-α-dehydroglucozaluzanin C, 10-α-hydroxy-8-dseoxyglucosid, 8-epideacylcynaropicrin, 8-epideacylcynaropicrin glucoside, glucozaluzanin C ixerin, picriside B and the like (M. Tamai et al., *Planta Med.*, 1989; S. Seo et al., *J. Am. Chem. Soc.*, 1981; T. Akihisa et al., *Phytochemistry*, 1994; W. Kisiel, *Phytochemistry*, 1992; H. Fuchino et al., *Chem. Pharm. Bull.*, 1995; K. Shiojima et al., *Chem. Pharm. Bull.*, 1996; A. Hisham et al., *Phytochemistry*, 1995).

In Korean Patent Registration Nos. 10-0721703 and 10-0769050, the present inventors confirmed the antiviral activity of *Alnus japonica* extracts. However, the *Alnus japonica* extracts have limited use, because they have a shortcoming in that they show antiviral activity only when they are administered at high concentrations.

Accordingly, the present inventors have made many efforts to develop a natural material, which has low toxicity to normal cells and shows an excellent effect of inhibiting viral proliferation even when it is administered at low concentrations. As a result, the present inventors found that triterpenoid-based compounds or diaryl hepatonoid-based compounds extracted from *Alnus japonica* show an excellent effect of inhibiting avian influenza virus activity, thereby completing the present invention.

DISCLOSURE OF INVENTION

It is an object of the present invention to provide a novel diaryl hepatonoid-based compound having excellent antiviral activity, its pharmaceutically acceptable salt, a hydrate, a solvate or a prodrug of any of the foregoing.

Another object of the present invention is to provide a pharmaceutical composition comprising said diaryl hepatonoid-based compound, its isomer or a pharmaceutically acceptable salt thereof; or a solvate, a hydrate or a prodrug of any of the foregoing as an active ingredient.

Still another object of the present invention is to provide the use of said diaryl hepatonoid-based compound having excellent antiviral activity; a pharmaceutically acceptable salt thereof; or a solvate, a hydrate or a prodrug of any of the foregoing.

To achieve the above objects, the present invention provides a novel diaryl hepatonoid-based compound of the following formula (1), its isomer or a pharmaceutically acceptable salt thereof; or a solvate, a hydrate or a prodrug of any of the foregoing:

[Formula 1]

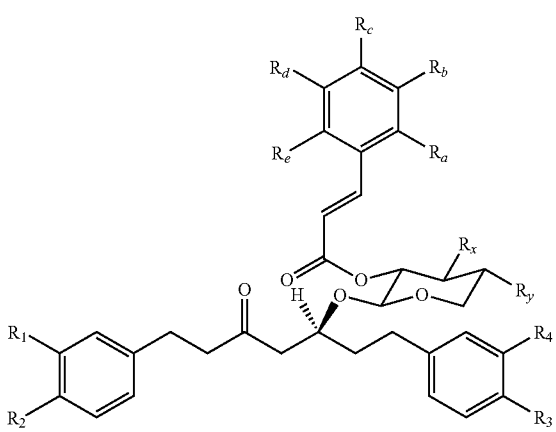

wherein $R_1$, $R_2$, $R_3$ and $R_4$ are each independently selected from the group consisting of hydrogen, hydroxyl, $C_1$-$C_6$ alkyl and $C_1$-$C_6$ alkoxy;

wherein $R_a$, $R_b$, $R_c$, $R_d$, and $R_e$ are each independently selected from the group consisting of hydrogen, hydroxyl, $C_1$-$C_6$ alkyl, $C_1$-$C_6$ alkoxy and —O—$R_f$, where $R_f$ is hydrogen or $C_1$-$C_6$ alkyl; and wherein $R_x$ and $R_y$ are hydrogen or hydroxyl.

The present invention also provides a composition for inhibiting viral activity, which comprises said novel diaryl hepatonoid-based compound of the following formula (1), its isomer or a pharmaceutically acceptable salt thereof; or a solvate, a hydrate or a prodrug of any of the foregoing as an active ingredient.

Other features and embodiments of the present invention will be more apparent from the following detailed descriptions and the appended claims.

BRIEF DESCRIPTION OF THE DRAWINGS

FIG. 1 is a schematic diagram showing a method of obtaining organic solvent fractions (12B-AJ-5A, 12B-AJ-5B, 12B-AJ-5C and 12B-AJ-5D), exhibiting antiviral activity, from the bark of *Alnus japonica*.

FIG. 2 is a schematic diagram showing a method of obtaining a 12B-AJ-17 fraction according to the present invention from a 12B-AJ-5C fraction by performing silica gel column chromatography.

BEST MODE FOR CARRYING OUT THE INVENTION

In one aspect, the present invention relates to diaryl hepatonoid-based compounds represented by the following formula (1):

[Formula 1]

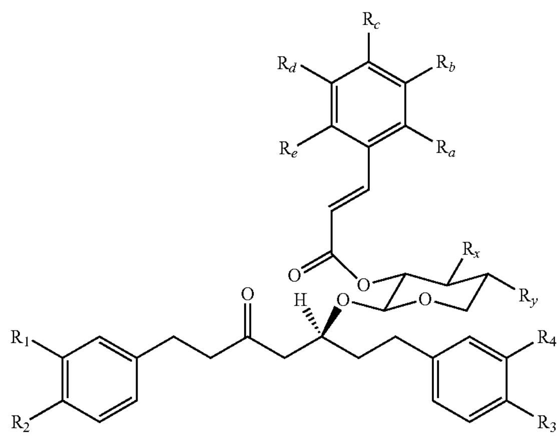

wherein $R_1$, $R_2$, $R_3$ and $R_4$ are each independently selected from the group consisting of hydrogen, hydroxyl, $C_1$-$C_6$ alkyl and $C_1$-$C_6$ alkoxy, preferably is hydrogen, hydroxyl, $C_1$-$C_3$ alkyl or $C_1$-$C_3$ alkoxy, more preferably is hydrogen or hydroxyl.

In the formula (1), $R_a$, $R_b$, $R_c$, $R_d$, and $R_e$ are each independently selected from the group consisting of hydrogen, hydroxyl, $C_1$-$C_6$ alkyl, $C_1$-$C_6$ alkoxy and —O—$R_f$, where $R_f$ is hydrogen or $C_1$-$C_6$ alkyl.

Preferably, at least one of $R_a$, $R_b$, $R_c$, $R_d$, and $R_e$ is hydroxyl; or any one of $R_a$, $R_b$, $R_c$, $R_d$, and $R_e$ is hydroxyl and another is —O—$R_f$.

In the formula (1), $R_x$ and $R_y$ are hydrogen or hydroxyl, preferably hydroxyl.

In the context of the present invention, "alkyl" is intended to include linear, branched, or cyclic hydrocarbon structures and combinations thereof. Lower alkyl refers to alkyl groups of from 1 to 6 carbon atoms. Examples of lower alkyl groups include methyl, ethyl, propyl, isopropyl, cyclopropyl, butyl, s- and t-butyl, cyclopropyl, cyclobutyl and the like. In the alkyl group in the present invention is preferably $C_1$-$C_6$ lower alkyl, and more preferably $C_1$-$C_3$ alkyl.

The term "alkoxy" refers to groups of from 1 to 8 carbon atoms of a straight, branched, cyclic configuration and combinations thereof attached to the parent structure through an oxygen. Examples thereof include methoxy, ethoxy, propoxy, isopropoxy, cyclopropyloxy, cyclohexyloxy and the like. In a preferred alkoxy group in the present invention is a lower alkoxy containing 1 to 4 carbon atoms.

Other terms have the same meaning as generally understood in the art to which the present invention pertains.

Typical examples of the compounds of formula (1) according to the present invention include (5S)-1,7-bis(3,4-dihydroxyphenyl)-3-heptanone-5-O-(2-coumaroyl)-β-D-xylopyranoside and (5S)-1,7-bis(3,4-dihydroxyphenyl)-3-heptanone-5-O-[2-(3-methoxycoumaroyl)]-β-D-xylopyranoside.

The compounds of the present invention may be prepared by separating pure compounds from organic solvent fractions, isolated from an *Alnus japonica* extract, as described below using a general technique known in the art.

Figure 2:
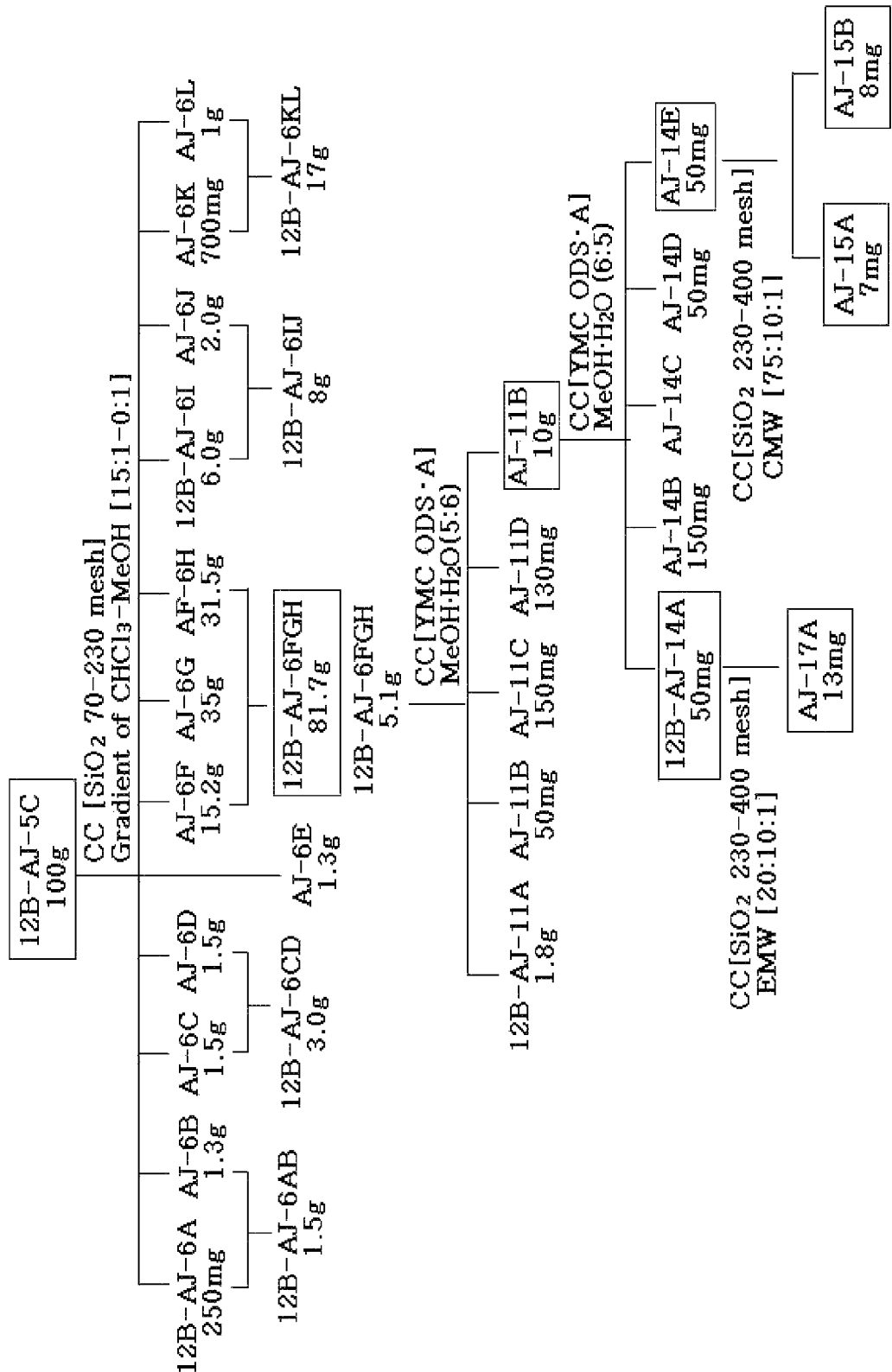

In one Example of the present invention, the bark of *Alnus japonica* (RNL BIO Co., Ltd., Korea) was sonicated three times in 95% ethanol at about 55° C., and then concentrated to obtain an ethanol fraction. Then, as shown in FIG. 1, the obtained fraction was fractionated again with ethanol, thereby obtaining an ethanol fraction (12B-AJ-5C). Then, the 12B-AJ-5C showing antiviral activity against avian influenza virus was subjected to repeated column chromatography as shown in FIG. 2, thereby obtaining a mixture, 12B-AJ-17A. 12B-AJ-17A1 and 12B-AJ-17A2, which constitute the mixture, were all identified as novel compounds.

Therefore, in one aspect, the present invention relates to a method of preparing the compound of formula (1). It is to be understood that the preparation methods below are merely the illustrative methods thereof and that the compounds of the present invention can be prepared by various methods based on the technology of the organic synthetic field. Thus, the scope of the present invention is not limited only thereto. For example, the synthesis of non-exemplified compounds according to the invention may be performed by modifications apparent to those skilled in the art, e.g., by appropriately protecting interfering groups, by changing to other suitable reagents known in the art, or by making routine modifications of reaction conditions. Alternatively, other reactions disclosed herein or known in the art will be recognized as having adaptability for preparing other compounds of the present invention.

Any person of ordinary skill in the art to which the present invention pertains can understand specific reactions conditions for preparing the compounds (1) according to the present invention through preparation examples and examples to be described later, and thus the detailed description thereof will be omitted herein.

In another aspect, the present invention relates to an isomer, a pharmaceutically acceptable salt, a solvate, a hydrate or a prodrug of the diaryl hepatonoid-based compound of formula (1).

The term "pharmaceutically acceptable salt" refers to a formulation of a compound that does not cause significant irritation to an organism to which it is administered and does not abrogate the biological activity and properties of the compound. The terms "hydrate", "solvate" and "isomer" have the same meanings as above. The pharmaceutically acceptable salt can be obtained by allowing the compound of the present invention to react with inorganic acids such as hydrochloric acid, bromic acid, sulfuric acid, nitric acid, phosphoric acid; sulfonic acids such as methanesulfonic acid, ethanesulfonic acid, and p-toluenesulfonic acid; or organic carbonic acids such as tartaric acid, formic acid, citric acid, acetic acid, trichloroacetic acid, trifluoroacetic acid, capric acid, isobutene acid, malonic acid, succinic acid, phthalic acid, gluconic acid, benzoic acid, lactic acid, fumaric acid, maleic acid and salicylic acid; hydrobromic acid and hydroiodic acid. Also, the salts may be obtained by allowing the compound of the present invention with bases to form with alkali metal bases such as ammonium salt, sodium salt or potassium salt; alkaline earth metal bases such as calcium salt and magnesium salt; salts with organic bases such as dicyclohexylamine, N-methyl-D-glucamine and tris(hydroxymethyl)methylamine; or salts with amino acids such as arginine and lysine.

The term "hydrate" refers to a compound of the present invention or a salt thereof, that further includes a stoichiometric or non-stoichiometric amount of water bound by non-covalent intermolecular forces.

The term "solvate" as used herein means a compound of the invention or a salt thereof, that further includes a stoichiometric or non-stoichiometric amount of a solvent bound by non-covalent intermolecular forces. Preferred solvents are volatile, non-toxic, and/or acceptable for administration to humans.

The term "isomer" means a compound of the present invention or a salt thereof, that has the same chemical formula or molecular formula but is optically or sterically different therefrom. For example, the compound of formula 1 of the present invention may have asymmetric centers on the choice of the substituents, and in this case, the compounds of formula 1 may exist as optical isomers such as enantiomers and diastereomers.

The term "prodrug" refers to an agent which is converted into the parent drug in vivo. Prodrugs are often useful because, in some situations, they may be easier to administer than the parent drug. They may, for instance, be bioavailable by oral administration whereas the parent drug is not. The prodrug may also have improved solubility in pharmaceutical compositions over the parent drug. An example of a prodrug, without limitation, would be a compound of the present invention which is administered as an ester ("prodrug") to facilitate transport across a cell membrane where water-solubility is detrimental to mobility, but which then is metabolically hydrolyzed to the carboxylic acid, the active entity, once inside the cell where water solubility is beneficial. A further example of the prodrug might be a short peptide (polyamino acid) bonded to an acidic group, where the peptide is metabolized to reveal the active moiety.

The term "compound according to the present invention" or "compound of formula (1)" unless otherwise indicated is intended to encompass all the compound itself, pharmaceutically acceptable salts, hydrates, solvates, isomers and prodrugs thereof.

The compounds of the present invention are effective for inhibition of viral activity, that is, treatment and prevention of diseases caused by influenza viruses. Particularly, the compounds of present invention show an excellent effect on the inhibition of the activity of influenza viruses, including human influenza virus, swine influenza virus, equine influenza virus, and avian influenza virus. The compounds of the present invention are particularly useful for prevention and treatment of diseases caused by infection with avian influenza virus.

Therefore, in another aspect, the present invention relates to a method of reducing or inhibiting viral activity by administering an effective amount of the compound of formula (1) to a patient. Namely, the present invention provides a method of treating and preventing diseases caused by viral activity using the compound of formula (1).

As used herein, the term "treating", unless otherwise indicated, means reversing, alleviating, inhibiting the progress of, or preventing the disorder or condition to which such term applies, or one or more symptoms of such disorder or condition. The term "treatment", as used herein, unless otherwise indicated, refers to the act of treating as "treating" is defined immediately above.

In another aspect, the present invention relates to a pharmaceutical composition comprising a therapeutically effective amount of the compound (1) and a pharmaceutically acceptable carrier thereof. The composition may, if necessary, additionally comprise a diluent, an excipient or the like.

The term "pharmaceutical composition" means a mixture of the compound of the present invention with other chemical components such as diluents or carriers.

The pharmaceutical composition facilitates administration of the compound to an organism. Multiple techniques of administering a compound exist in the art including, but not limited to, oral, injection, aerosol, parenteral, and topical administration. Pharmaceutical compositions can also be obtained by reacting compounds with inorganic or organic acids such as hydrochloric acid, hydrobromic acid, sulfuric acid, nitric acid, phosphoric acid, methanesulfonic acid, p-toluenesulfonic acid, salicylic acid and the like.

As used herein, the term "therapeutically effective amount" means the amount of active ingredient effective to alleviate or remove one or more symptoms of the disorder to be treated, or to delay clinical markers or the initiation of symptoms of the disease to be prevented. Thus, the therapeutically effective amount means the amount having the effect of (1) reversing the rate of progress of the disease decreasing the size of a tumor in the case of cancer, (2) prohibiting further progress of the disease or delaying the progression of cancer preferably arresting tumor metastasis and/or (3) alleviating (preferably, removing) one or more symptoms associated with the disease.

The term "carrier" defines a chemical compound that facilitates the incorporation of a compound into cells or tissues. For example dimethyl sulfoxide (DMSO) is a commonly utilized carrier as it facilitates the uptake of many organic compounds into the cells or tissues of an organism.

The term "diluent" defines chemical compounds diluted in water that will dissolve the compound of interest as well as stabilize the biologically active form of the compound. Salts dissolved in buffered solutions are utilized as diluents in the art. One commonly used buffered solution is phosphate buffered saline because it mimics the salt conditions of human blood. Since buffer salts can control the pH of a solution at low concentrations, a buffered diluent rarely modifies the biological activity of a compound.

The term "physiologically acceptable" defines a carrier or diluent that does not abrogate the biological activity and properties of the compound.

The compound used herein may be administered as the compound per se or as a pharmaceutical composition comprising the compound with other active ingredients in the combination therapy or with other suitable carriers or excipients, to the human patient.

(a) Administration Route

Suitable routes of administration may, for example, include oral, nasal, transmucosal, or intestinal administration; parenteral delivery, including intramuscular, subcutaneous, intravenous, intramedullary injections, as well as direct intraventricular, intraperitoneal, or intraocular injections.

Alternately, one may administer the compound in a local rather than systemic manner, for example, via injection of the compound directly in a solid tumor, often in a depot or sustained release formulation. Furthermore, one may administer the drug in a targeted drug delivery system, for example, in a liposome coated with a tumor-specific antibody. The liposomes will be targeted to and taken up selectively by the tumor.

(b) Composition/Formulation

The pharmaceutical composition of the present invention may be prepared in a manner that is itself known, e.g. by means of conventional mixing, dissolving, granulating, dragee-making, powdering, emulsifying, encapsulating, entrapping or lyophilizing processes.

Thus, pharmaceutical compositions for use in accordance with the present invention may be formulated in conventional manner using one or more physiologically acceptable carriers comprising excipients and auxiliaries which facilitate processing of the active compounds into preparations which can be used pharmaceutically. Proper formulation is dependent upon the route of administration chosen. Any of the well-known techniques, carriers, and excipients may be used as suitable and as understood in the art; e.g., in Remington's Pharmaceutical Sciences, above.

For injection, the agents of the present invention may be formulated in aqueous solutions or lipid emulsions, preferably in physiologically compatible buffers such as Hanks's solution, Ringer's solution, or physiological saline buffer. For transmucosal administration, penetrants appropriate to the barrier to be permeated are used in the formulation. Such penetrants are generally known in the art.

For oral administration, the compounds can be formulated readily by combining the active compounds with pharmaceutically acceptable carriers well known in the art. Such carriers enable the compounds of the present invention to be formulated as tablets, pills, dragees, capsules, liquids, gels, syrups, slurries, suspensions and the like, for oral ingestion by a patient to be treated. Pharmaceutical preparations for oral use can be obtained by mixing one or more solid excipient with pharmaceutical combination of the invention, optionally grinding the resulting mixture, and processing the mixture of granules, after adding suitable auxiliaries, if desired, to obtain tablets or dragee cores. Suitable excipients are, in particular, fillers such as sugars, including lactose, sucrose, mannitol, or sorbitol; cellulose preparations such as, for example, maize starch, wheat starch, rice starch, potato starch, gelatin, gum tragacanth, methyl cellulose, hydroxypropylmethyl-cellulose, sodium carboxymethylcellulose, and/or polyvinylpyrrolidone (PVP). If desired, disintegrating agents may be added, such as the cross-linked polyvinyl pyrrolidone, agar, or alginic acid or a salt thereof such as sodium alginate.

Dragee cores are provided with suitable coatings. For this purpose, concentrated sugar solutions may be used, which may optionally contain gum arabic, talc, polyvinyl pyrrolidone, carbopol gel, polyethylene glycol, and/or titanium dioxide, lacquer solutions, and suitable organic solvents or solvent mixtures. Dyestuffs or pigments may be added to the tablets or dragee coatings for identification or to characterize different combinations of active compound doses.

Pharmaceutical preparations which can be used orally include push-fit capsules made of gelatin, as well as soft, sealed capsules made of gelatin and a plasticizer, such as glycerol or sorbitol. The push-fit capsules can contain the active ingredients in admixture with filler such as lactose, binders such as starches, and/or lubricants such as talc or magnesium stearate and, optionally, stabilizers. In soft capsules, the active compounds may be dissolved or suspended in suitable liquids, such as fatty oils, liquid paraffin, or liquid polyethylene glycols. In addition, stabilizers may be added. Furthermore, the formulations of the present invention may be coated with enteric polymers. All formulations for oral administration should be in dosages suitable for such administration.

For buccal administration, the compositions may take the form of tablets or lozenges formulated in conventional manner.

For administration by inhalation, the compounds for use according to the present invention are conveniently delivered in the form of an aerosol spray presentation from pressurized packs or a nebuliser, with the use of a suitable propellant, e.g., dichlorodifluoromethane, trichlorofluoromethane, dichlorotetrafluoroethane, carbon dioxide or other suitable gas. In the case of a pressurized aerosol the dosage unit may be determined by providing a valve to deliver a metered amount. Capsules and cartridges of, e.g., gelatin for use in an inhaler or insufflator may be formulated containing a powder mix of the compound and a suitable powder base such as lactose or starch.

The compounds may be formulated for parenteral administration by injection, e.g., by bolus injection or continuous infusion. Formulations for injection may be presented in unit dosage form, e.g., in ampoules or in multi-dose containers, with an added preservative. The compositions may take such forms as suspensions, solutions or emulsions in oily or aqueous vehicles, and may contain formulatory agents such as suspending, stabilizing and/or dispersing agents.

Pharmaceutical formulations for parenteral administration include aqueous solutions of the active compounds in water-soluble form. Additionally, suspensions of the active compounds may be prepared as appropriate oily injection suspensions. Suitable lipophilic solvents or vehicles include fatty oils such as sesame oil, or synthetic fatty acid esters, such as ethyl oleate or triglycerides, or liposomes. Aqueous injection suspensions may contain substances which increase the viscosity of the suspension, such as sodium carboxymethyl cellulose, sorbitol, or dextran. Optionally, the suspension may also contain suitable stabilizers or agents which increase the solubility of the compounds to allow for the preparation of highly concentrated solutions.

Alternatively, the active ingredient may be in powder form for constitution with a suitable vehicle, e.g., sterile pyrogen-free water, before use.

The compounds may also be formulated in rectal compositions such as suppositories or retention enemas, e.g., containing conventional suppository bases such as cocoa butter or other glycerides.

In addition to the formulations described previously, the compounds may also be formulated as a depot preparation. Such long acting formulations may be administered by implantation (for example subcutaneously or intramuscularly) or by intramuscular injection. Thus, for example, the compounds may be formulated with suitable polymeric or hydrophobic materials (for example as an emulsion in an acceptable oil) or ion exchange resins, or as sparingly soluble derivatives, for example, as a sparingly soluble salt.

A pharmaceutical carrier for the hydrophobic compounds of the present invention is a co-solvent system comprising benzyl alcohol, a nonpolar surfactant, a water-miscible organic polymer, and an aqueous phase. A common co-solvent system used is the VPD co-solvent system, which is a solution of 3% w/v benzyl alcohol, 85 w/v of the nonpolar surfactant Polysorbate 80™, and 65% w/v polyethylene glycol 300, made up to volume in absolute ethanol. VPD co-solvent system (VPD:D5W) consists of 1:1-diluted VPD by 5% testrose in solution. Naturally, the proportions of a co-solvent system may be varied considerably without destroying its solubility and toxicity characteristics. Furthermore, the identity of the co-solvent components may be varied: for example, other low-toxicity nonpolar surfactants may be used instead of POLYSORBATE 80 the fraction size of polyethylene glycol may be varied; other biocompatible polymers may replace polyethylene glycol, e.g., polyvinyl pyrrolidone; and other sugars or polysaccharides may substitute for dextrose.

Alternatively, other delivery systems for hydrophobic pharmaceutical compounds may be employed. Liposomes and emulsions are well known examples of delivery vehicles or carriers for hydrophobic drugs. Certain organic solvents such as dimethylsulfoxide also may be employed, although usually at the cost of greater toxicity. Additionally, the compounds may be delivered using a sustained-release system, such as semipermeable matrices of solid hydrophobic polymers containing the therapeutic agent. Various sustained-release materials have been established and are well known by those skilled in the art. Sustained-release capsules may, depending on their chemical nature, release the compounds for 2-3 weeks up to over 100 days. Depending on the chemical nature and the biological stability of the therapeutic reagent, additional strategies for protein stabilization may be employed.

Many of the compounds of the present invention may be provided as salts with pharmaceutically compatible counterions. Pharmaceutically compatible salts may be formed with many acids, including but not limited to hydrochloric, sulfuric, acetic, lactic, tartaric, malic, succinic, etc. Salts tend to be more soluble in aqueous or other protonic solvents than are the corresponding free acid or base forms.

(c) Effective Amount

Pharmaceutical compositions suitable for use in the present invention include compositions where the active ingredients are contained in an amount effective to achieve its intended purpose. More specifically, a therapeutically effective amount means an amount of compound effective to prevent, alleviate or ameliorate symptoms of disease or prolong the survival of the subject being treated. Determination of a therapeutically effective amount is well within the capability of those skilled in the art, especially in light of the detailed disclosure provided herein.

For any compound used in the inventive methods, the therapeutically effective dose can be estimated initially from cell culture assays. A dose can also be calculated in animal models to achieve a circulating plasma concentration range that includes the $IC_{50}$ as determined in cell culture. Such information can be used to more accurately determine useful doses in humans.

Toxicity and therapeutic efficacy of the compounds described herein can be determined by standard pharmaceutical procedures, using either cells in culture or experimental animals to determine the LD50 (the dose lethal to 50% of the population) and the ED50 (the dose therapeutically effective in 50% of the population). The dose ratio between toxic and therapeutic effects is the therapeutic index and it can be expressed as the ratio between LD50 and ED50. Compounds that exhibit high therapeutic indices are preferred. The data obtained from the cell culture assays can be used in formulating a range of dosage for use in humans. The dosage of such compounds lies preferably within a range of circulating concentrations that include the ED50 with little or no toxicity. The dosage may vary within this range depending upon the dosage form employed and the route of administration utilized. The exact formulation, route of administration and dosage for the pharmaceutical compositions of the present invention can be chosen by the individual physician in view of the patient's condition (See e.g., Fingl et al. 1975, in "The Pharmacological Basis of Therapeutics", Ch. 1, p. 1). Typically, the dose range of the composition administered to the patient can be from about 0.5 to 1000 mg/kg of the patient's body weight. The dosage may be a single one or a series of two or more given in the course of one or more days, as is needed by the patient.

Dosage amount and interval may be adjusted individually to provide plasma levels of the active moiety which are sufficient to maintain the kinase modulating effects, or minimal effective concentration (MEC). The MEC will vary for each compound but can be estimated from in vitro data, e.g. the concentration necessary to achieve a 50-90% inhibition of kinase using the assays described herein. However, HPLC assays or bioassays can be used to determine plasma concentrations. Dosages necessary to achieve the MEC will depend on individual characteristics and route of administration. Compounds should be administered using a regimen which maintains plasma levels above the MEC for 10-90% of the time, preferably between 30-90% and most preferably between 50-90%. Dosages necessary to achieve the MEC will depend on individual characteristics and route of administration.

In cases of local administration or selective uptake, the effective local concentration of the drug may not be related to plasma concentration.

The amount of composition administered will, of course, be dependent on the subject being treated, on the subject's weight, the severity of the affliction, the manner of administration and the judgment of the prescribing physician.

EXAMPLES

Hereinafter, the present invention will be described in further detail with reference to the following examples. It will be obvious to a person having ordinary skill in the art that these embodiments are merely for illustrative purposes, and the scope of the present invention should not be construed as being limited to the above described embodiments.

Example 1

Preparation of *Alnus japonica* Extracts 3.5 kg of the bark of *Alnus japonica* (RNL BIO Co., Ltd.) was added to 9 L of 95% ethanol, sonicated three times at 55° C., and then concentrated, thus obtaining 900 g of an ethanol fraction (12B-AJ-5A). As shown in FIG. 1, the obtained 12B-AJ-5A fraction was fractionated sequentially with $CH_2Cl_2$ and ethanol to obtain a dichloromethane ($CH_2Cl_2$) fraction (12B-AJ-5B, 139 g), an ethanol fraction (12B-AJ-5C, 400 g) and a water fraction (12B-AJ-5D).

Example 2

Measurement of Antiviral Activities of *Alnus japonica* Extract and Compounds Derived from *Alnus japonica* Extract In order to measure the antiviral activities of the *Alnus japonica* extract and *Alnus japonica* extract-derived compounds, KBNP-0028 (KCTC 10866BP) having excellent proliferation ability was used as avian influenza virus. Herein, KBNP-0028 (KCTC 10866BP) was obtained by subculturing A/chicken/Korea/SNU0028/2000(H9N2), isolated in Korea in 2000, and cloning the cultured virus.

For cultivation of hatchery egg shell pieces, the egg shell of 10-11 day-old SPF hatchery eggs (Sunrise Co., NY) was washed with 70% ethanol, and the chick embryo and body fluid were removed. The resulting egg shell was cut to a size of about 8 mm×8 mm such that the chorioallantoic membrane attached to the inner surface of the egg shell was not detached. The cut egg shell piece was added to each well of a 24-well culture plate. The culture medium used in this experiment was prepared by mixing 199 medium (GIBCO-BRL, NY, USA) with F10 medium (GIBCO-BRL, NY, USA) at a ratio of 1:1 and adding 0.075% sodium bicarbonate and 100 µg/ml gentamicin thereto.

The undiluted allantoic fluid of KBNP-0028 prepared as described above was 4-10-fold diluted and 100 µl of the diluted fluid was added to the chorioallantoic membrane surface of the shell pieces of the 10-11-day-old embryonated eggs and then cultured at 37° C. for 30 minutes, thereby infecting the egg pieces with the virus. 1,000 µl of the above-prepared culture medium was added to each well of the culture plate, and then the *Alnus japonica* extract was added thereto at various concentrations. The virus-infected solutions, to which various concentrations of the *Alnus japonica* extract had been added, were cultured at 37° C. for 7 days.

The cultured broths were collected and subjected to a plate hemagglutination test. For this purpose, 25 µl of each of the culture broths (having concentrations of 15.6, 31.3, 62.5, 125, 250 and 500 µg/ml, respectively) and 25 µl of washed chicken red blood cells (0.1%) were added to 24-well plates and mixed evenly. The plates were moved vertically and horizontally, and whether hemagglutination occurred within 2 minutes after the movement was examined to determine the proliferation of the virus.

Preparation Example 1

Isolation and Purification of (5S)-1,7-bis(3,4-dihydroxyphenyl)-3-heptanone-5-O-(2-coumaroyl)-β-D-xylopyranoside The 12B-AJ-5C fraction obtained in Example 1 was subjected to repeated column chromatography as shown in FIG. 2, thereby obtaining a pure compound, 12B-AJ-17A (13.0 mg). Then, a novel compound of 12B-AJ-17A-1[(5S)-1,7-bis(3,4-dihydroxyphenyl)-3-heptanone-5-O-(2-coumaroyl)-β-D-xylopyranoside] having the following chemical structure was obtained from the compound 12B-AJ-17A:

[Formula 2]

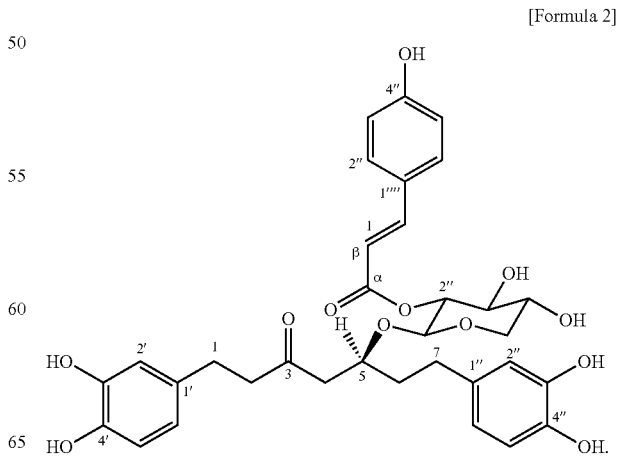

Table 1 below shows the results of analyzing the compound (5S)-1,7-bis(3,4-dihydroxyphenyl)-3-heptanone-5-O-(2-coumaroyl)-β-D-xylopyranoside.

TABLE 1

| Carbon No. | $^{13}$C (125 MHz, CD$_3$OD) | $^1$H (500 MHz, CD$_3$OD) |
|---|---|---|
| Diaryl heptane moiety | | |
| 1 | 30.26 | 2.50-2.60 (2H, overlapped) |
| 2 | 46.50 | 2.48 (1H, overlapped), 2.58 (1H, oveplapped |
| 3 | 211.04 | |
| 4 | 49.10$^a$ | 2.44 (1H, m), 2.66 (1H, m) |
| 5 | 77.32 | 4.08 (1H, m) |
| 6 | 38.69 | 1.70 (1H, m), 1.80 (1H, m) |
| 7 | 31.79 | 2.45-2.50 (2H, m)2H2H |
| 1' | 133.92 | |
| 2' | 116.72 | 6.61 (1H, d, J = 2.0) |
| 3' | 146.27 | |
| 4' | 144.57 | |
| 5' | 116.49 | 6.64 (1H, d, J = 8.0) |
| 6' | 120.67 | 6.47 (1H, dd, J = 8.0, 2.0) |
| 1'' | 135.24 | |
| 2'' | 116.65 | 6.61 (1H, d, J = 2.0) |
| 3'' | 146.20 | |
| 4'' | 144.31 | |
| 5'' | 116.49 | 6.64 (1H, d, J = 8.0) |
| 6'' | 120.61 | 6.47 (1H, brd, J = 8.0) |
| Xylose | | |
| 1''' | 103.42 | 4.49 (1H, d, J = 7.5) |
| 2''' | 75.45 | 4.74 (1H, t, J = 7.0) |
| 3''' | 76.39 | 3.52 (1H, t, J = 9.0) |
| 4''' | 71.51 | 3.58 (1H, m) |
| 5''' | 67.10 | 3.24 (1H, t, J = 11.0), 3.93 (1H, dd, J = 11.5, 5.5) |
| Coumaroyl | | |
| 1'''' | 127.23 | |
| 2'''' | 131.41 | 7.40 (1H, d, J = 8.0) |
| 3'''' | 117.05 | 6.78 (1H, d, J = 8.0) |
| 4'''' | 161.48 | |
| 5'''' | 117.05 | 6.78 (1H, d, J = 8.0) |
| 6'''' | 131.41 | 7.40 (1H, d, J = 7.5) |
| C-α | 168.46 | |
| C-β | 115.39 | 6.30 (1H, d, J = 15.5) |
| C-γ | 147.05 | 7.62 (1H, d, J = 15.5) | overlapped with solvent signals 1H (v), 13C (v), COSY(v), HMQC (v), HMBC (v)

Preparation Example 2

Isolation and Purification of (5S)-1,7-bis(3,4-dihydroxyphenyl)-3-heptanone-5-O-[2-(3-methoxycoumaroyl)]-β-D-xylopyranoside The 12B-AJ-5C fraction was subjected to repeated column chromatography as shown in FIG. 2, thereby obtaining a pure compound, 12B-AJ-17A (13.0 mg). Then, a novel compound of 12B-AJ-17A-2[(5S)-1,7-bis(3,4-dihydroxyphenyl)-3-heptanone-5-O-[2-(3-methoxycoumaroyl)]-β-D-xylopyranoside] having the following chemical structure was obtained from the compound 12B-AJ-17A:

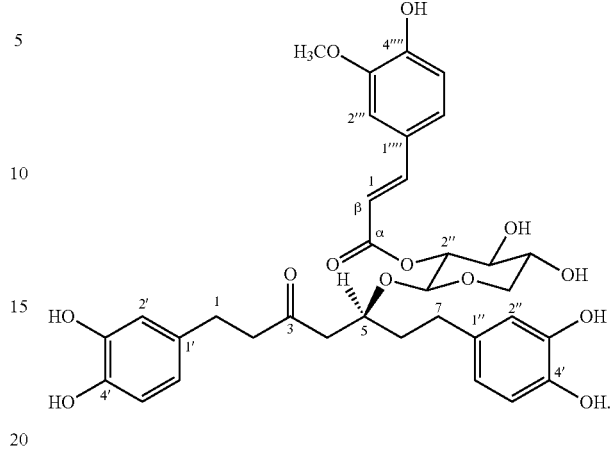

[Formula 3]

Table 2 below shows the results of analyzing the compound (5S)-1,7-bis(3,4-dihydroxyphenyl)-3-heptanone-5-O-[2-(3-methoxycoumaroyl)]-β-D-xylopyranoside.

TABLE 2

| Carbon No. | $^{13}$C (125 MHz, CD$_3$OD) | $^1$H (500 MHz, CD$_3$OD) |
|---|---|---|
| Diaryl heptane moiety | | |
| 1 | 30.26 | 2.50-2.60 (2H, overlapped) |
| 2 | 46.44 | 2.52 (1H, overlapped), 2.61 (1H, overlapped) |
| 3 | 211.11 | |
| 4 | 49.20$^a$ | 2.41 (1H, m), 2.62 (1H, m) |
| 5 | 77.18 | 4.08 (1H, m) |
| 6 | 38.69 | 1.70 (1H, m), 1.80 (1H, m) |
| 7 | 31.79 | 2.45-2.50 (2H, m)2H2H |
| 1' | 133.96 | |
| 2' | 116.65 | 6.61 (1H, d, J = 2.0) |
| 3' | 146.27 | |
| 4' | 144.57 | |
| 5' | 116.39 | 6.64 (1H, d, J = 8.0) |
| 6' | 120.67 | 6.47 (1H, dd, J = 8.0, 2.0) |
| 1'' | 135.24 | |
| 2'' | 116.59 | 6.61 (1H, d, J = 2.0) |
| 3'' | 146.20 | |
| 4'' | 144.31 | |
| 5'' | 116.49 | 6.64 (1H, d, J = 8.0) |
| 6'' | 120.83 | 6.47 (1H, brd, J = 8.0) |
| Xylose | | |
| 1''' | 103.28 | 4.48 (1H, d, J = 8.0) |
| 2''' | 75.45 | 4.74 (1H, t, J = 7.0) |
| 3''' | 76.39 | 3.52 (1H, t, J = 9.0) |
| 4''' | 71.51 | 3.58 (1H, m) |
| 5''' | 67.10 | 3.24 (1H, t, J = 11.0), 3.93 (1H, dd, J = 11.5, 5.5) |
| 3-Methoxycoumaroyl | | |
| 1'''' | 127.78 | |
| 2'''' | 111.91 | 7.12 (1H, d, J = 1.5) |
| 3'''' | 149.51 | |
| 4'''' | 150.83 | |
| 5'''' | 116.59 | 6.80 (1H, d, J = 8.0) |
| 6'''' | 124.28 | 7.04 (1H, dd, J = 8.0, 1.5) |
| C-α | 168.50 | |
| C-β | 115.73 | 6.35 (1H, d, J = 15.5) |
| C-γ | 147.30 | 7.62 (1H, d, J = 15.5) |
| OCH$_3$ | 56.56 | 3.82 (3H, s) |

Example 3

Analysis of Antiviral Activities and Cytotoxicities of Novel Diaryl Hepatonoid-Based Compounds Isolated from *Alnus japonica* Extract In order to examine the antiviral activities and cytotoxicities of the *Alnus japonica* extract-derived novel diaryl hepatonoid-based compounds prepared, the virus inhibitory activities of the diaryl hepatonoid-based compounds were measured according to the viral activity measurement method of Example 2, and the cytotoxicities of the compounds were analyzed by an MTT assay using CEF (chicken embryo fibroblasts) (Tables 3 and 4).

As a result, it was found that the 12B-AJ-17A-1 fraction had antiviral activity and showed no cytotoxicity even at a concentration of 100 µg/mL.

TABLE 3

Antiviral activities of *Alnus japonica* extract-derived diaryl hepatonoid-based compounds

| fraction | Number of wells wherein hemagglutination occurs (among 6 wells) | | | |
|---|---|---|---|---|
| | 12.5(µg/mL) | 25(µg/mL) | 50(µg/mL) | 100(µg/mL) |
| 12B-AJ-17A-1 | 3 | 3 | 3 | 3 |
| control | 10(0) | 10(−1) | 10(−2) | 10(−3) |
| | 6 | 6 | 4 | 0 |

TABLE 4

Analysis of cytotoxicities of *Alnus japonica* extract-derived diaryl hepatonoid-based compounds

| fraction | Concentration(µg/mL) | | | | |
|---|---|---|---|---|---|
| | 6.25 | 12.5 | 25 | 50 | 100 |
| 12B-AJ-17A-1 | 0.459 | 0.453 | 0.453 | 0.580 | 0.434 |
| | | | 0.425 ± 0.014 | | |

INDUSTRIAL APPLICABILITY

As described above in detail, the compounds of formula (1) according to the present invention will be useful for the treatment and/or prevention of diseases caused by virus activity. Particularly, the compounds of the present invention are useful for inhibiting the activity of avian influenza virus.

Although the present invention has been described in detail with reference to the specific features, it will be apparent to those skilled in the art that this description is only for a preferred embodiment and does not limit the scope of the present invention. Thus, the substantial scope of the present invention will be defined by the appended claims and equivalents thereof.

The invention claimed is:

1. An isolated compound of the following formula (1) for inhibiting virus activity, or its isomer, pharmaceutically acceptable salt, solvate, or hydrate thereof:

[Formula 1]

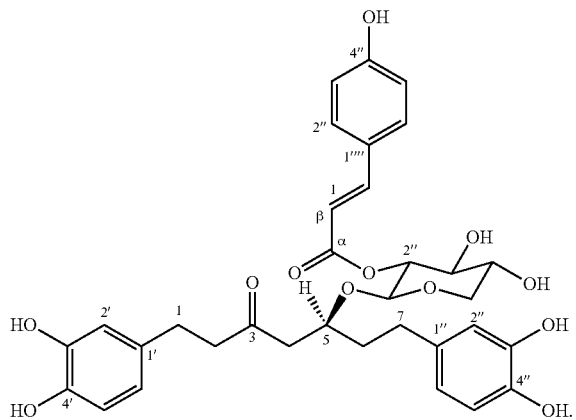

2. The compound, its isomer, pharmaceutically acceptable salt, solvate, or hydrate according to claim 1, wherein the virus is influenza virus.

3. The compound, its isomer, pharmaceutically acceptable salt, solvate, or hydrate according to claim 2, wherein the virus is avian influenza virus.

* * * * *